(12) United States Patent
Keech et al.

(10) Patent No.: US 7,547,770 B2
(45) Date of Patent: Jun. 16, 2009

(54) COLOSTRAL FRACTIONATION PROCESS

(75) Inventors: Andrew Keech, Scottsdale, AZ (US); Rafael Jimenez-Flores, San Luis Obispo, CA (US)

(73) Assignee: Advanced Protein Systems, Phoenix, AZ (US)

( * ) Notice: Subject to any disclaimer, the term of this patent is extended or adjusted under 35 U.S.C. 154(b) by 178 days.

(21) Appl. No.: 10/981,152

(22) Filed: Nov. 3, 2004

(65) Prior Publication Data

US 2005/0092684 A1 May 5, 2005

Related U.S. Application Data

(60) Provisional application No. 60/516,674, filed on Nov. 3, 2003.

(51) Int. Cl.
C07K 14/00 (2006.01)
A23J 1/20 (2006.01)

(52) U.S. Cl. .................... 530/417; 424/157.1

(58) Field of Classification Search ............ None
See application file for complete search history.

(56) References Cited

U.S. PATENT DOCUMENTS

| | | | |
|---|---|---|---|
| 4,091,116 A | | 5/1978 | Edwards et al. |
| 4,497,836 A | | 2/1985 | Marquardt et al. |
| 4,668,771 A | * | 5/1987 | Kawakami et al. .......... 530/366 |
| 4,689,151 A | | 8/1987 | Kosikowski et al. |
| 4,997,914 A | * | 3/1991 | Kawakami et al. .......... 530/395 |
| 5,149,647 A | * | 9/1992 | Burling ...................... 435/192 |
| 5,290,685 A | * | 3/1994 | Koide et al. ................. 435/68.1 |
| 6,010,698 A | | 1/2000 | Kussendrager et al. |
| 6,096,870 A | * | 8/2000 | Mozaffar et al. ............ 530/366 |
| 6,139,746 A | * | 10/2000 | Kopf .......................... 210/635 |
| 6,852,700 B1 | * | 2/2005 | Janusz et al. ................. 514/21 |
| 6,903,068 B1 | * | 6/2005 | Stanton et al. ............... 514/2 |
| 2002/0127279 A1 | | 9/2002 | Matthews |
| 2004/0266681 A1 | | 12/2004 | Boldogh et al. |

FOREIGN PATENT DOCUMENTS

| WO | WO 98/14473 | * | 4/1998 |
|---|---|---|---|
| WO | WO 0075173 | | 12/2000 |

OTHER PUBLICATIONS

Shing et al., "Purification of polypeptide growth factors from milk", Methods in Enzymology 146: 42-48 (1987).*

Ion Exchange Chromatography, principles and methods, Chpt. 7, 29-38 (1980) (Pharmacia Fine Chemicals).*

Cechova, D., "Trypsin inhibitor from cow colostrum", Methods Enzymology 45: 806-813 (1976).*

Riediker et al., "Analysis of beta-lactam antibiotics in incurred raw milk by rapid test methods and liquid chromatography coupled with electrospray ionization tandem mass spectrometry", J. Agric. Food Chem. 49: 4171-4176 (2001).*

Janusz et al., "Immunoglobulins of colostrum", Achivum Immunologiae Et Therapiae Experimentalis 21: 435-444 (1973).*

Takayama et al, Factors in Bovine Colostrum that Enhance the Migration of Human Fibroblasts in Type I Collagen Gels, Biosci. Biotech. Biochem. 2001 vol. 65, No. 12, pp. 2776-2779.

Janusz et al., Chemical and Physical Characterization of a Proline-Rich Polypeptide from Sheep Colostrum, Biochem. J. 1981 vol. 199, pp. 9-15.

Kruzel et al., The Alcohol-Induced Conformational Changes in Casein Micelles: A New Challenge for the Purification of Colostrinin, The Protein Jour., 2004 V 23 No. 2, pp. 127-133.

Inglot, et al.: "Colostrinine: a proline-rich polypeptide from ovine colostrum is a modest cytokine inducer in human leukocytes," Archivum Immunologiae et Therapiae Experimentalis, 1996, vol. 44, pp. 215-224.

Staroscik, Krystyna et al.:"Immunologically active nonapeptide fragment of a proline-rich polypeptide from ovine colostrum: amino acid sequence and immunoregulatory properties," Molecular Immunology, 1983, vol. 20 (12), pp. 1277-1282.

Uruakpa, et al.: "Colostrum and its benefits: a review," Nutrition Research, 2002, vol. 22, pp. 755-767.

* cited by examiner

*Primary Examiner*—Anand U Desai
(74) *Attorney, Agent, or Firm*—Stanley A. Kim, P.A.; Stanley A. Kim

(57) ABSTRACT

A method (100) and a system (200) for processing mammalian bodily fluids to isolate target peptides and proteins. The method can include the steps of passing a mammalian bodily fluid through at least one ion exchange column (204). The ion exchange column can include an anionic resin and/or a cationic resin. The ion exchange column can be selected to remove large particles at a first pH level selected to remove such large particles at a maximum fluid pressure of 30 pounds per square inch (psi), for example less than 10 psi. The large particles can be released from the ion exchange column with a rinse solution having a pH selected for releasing the large particles. The pH of the fluid then can be adjusted to be a value less than 5.0, and the fluid can be filtered with a microfilter or ultrafilter (210).

5 Claims, 2 Drawing Sheets

COLOSTRAL FRACTIONATION PROCESS

CROSS REFERENCES TO RELATED APPLICATIONS

This application claims benefit of U.S. provisional patent application Ser. No. 60/516,674, filed Nov. 3, 2003, which is herein incorporated by reference.

BACKGROUND OF THE INVENTION

1. Statement of the Technical Field

The present invention relates to nutritional compositions, and more particularly to nutritional compositions that are derived from colostrum of animals.

2. Description of the Related Art

Since the early 1970's whey proteins have been concentrated for uses in healthcare and for use in nutritional and functional foods, for example as an ingredient. These proteins include beta-lactoglobulin and alpha-lactalbumin, which are commonly extracted from bovine milk. More recently, lactoferrin and immunoglobulins also have been extracted from bovine milk, but to a lesser extent. Although the concentrations of lactoferrin (100-200 mg/liter) and the immunoglobulins (5-6% of total whey proteins) are low in milk, the concentrations of lactoferrin (1-2 g/liter), proline-rich polypeptides and immunoglobulins (70-80% of total whey proteins) are much higher in colostrum.

Some protein functions involve the binding of other molecules called ligands. Ligands can be drugs, hormones or antigens that can bind with proteins. Those compounds that can act as ligands but which normally are found naturally in animal bodies fall into three general classes: neurotransmitters, steroids (including the sex hormones), and peptides. The first two classes are considered to be bioactive, whereas peptides are not. (Bioactive is a phrase that describes a set of compounds which have an effect on animal cells that is in direct proportion to their number and which are produced either outside the body of the animal or only in specialized organs or systems thereof.) Peptides typically have a relatively low molecular weight and are the product of the sequential covalent bonding of several amino acids. For example, peptides typically are formed from about 4 to 100 sequentially bonded amino acids.

Proline-rich-peptides and/or non-ionic peptides are important in various biochemical processes. These peptides may be termed receptor peptides and are in fact very specialized types of proteins. They are believed to reside in or on the exterior surfaces of all animal cells (regardless of particular cellular function). When activated through interaction with a ligand, a receptor then transmits a biochemical message into the interior of the cell.

Peptides, such as proline-rich-peptides and non-ionic peptides, which function as ligands are produced in the ribosomes of all or very nearly all of the cells of animals and man. They are sometimes referred to as informational peptides because they often provide little or no nutritional value, but contain specific information to help trigger specific biological processes. The informational peptides also may help protect cells by re-orientating receptor sites often used by synthetic viral protein ligands. Thus, these peptides may help inhibit viruses from attaching themselves to those specific individual target cells by regulating immuno-modular and cytokine intercellular function and intracellular function.

Peptides generally are relatively small, at least in relation to most proteins which tend to have molecular weights of at least 20,000 Daltons. In general, peptides have a molecular weight of no more than about 1000 Daltons, although some might be larger, even perhaps as large as about 6000 Daltons. Nevertheless, they are significantly smaller than most proteins.

When a peptide leaves the cell in which it was produced, it moves throughout the body by way of the interstitial fluids between the cells and the circulatory system. In the blood and interstitial fluids, peptides tend not to agglomerate with themselves (i.e., they remain separate). This separateness allows the peptides to remain in forms in which they can bind with appropriate receptors. For instance, a peptide produced by one cell can be transported to and interact with the cellular function of a distant cell. When such an interaction occurs, a type of biochemical transmission to the cell interior is set into motion and this, in turn, induces some type of a response within the cell. One such cellular action is believed to be the production of additional peptides of the type bound to the cellular receptor.

As mentioned previously, some viruses take up residence in animal bodies by entering cells through particular types of receptors. If the necessary type of receptor already is bound to another ligand, such as a peptide, or the shape of the receptor does not or is no longer compatible with the viral ligand, then the virus cannot enter that given cell and must find another cell in which to enter. If all cells have the target receptor bound with other ligands, or there has been a conformational change of shape at the receptor site because of biochemical processes from within the cell, the virus' entry path is blocked and infection is averted.

When an animal, including a human, is healthy, it has a full (or very nearly full) complement of peptides. However, due to any one or more of a variety of factors, such as increased age of the animal, bodily abuse by environment or substance abuse, nutrition, suppressed immune system, and/or illnesses and diseases, an animal may fail to produce or maintain one or more of these types of peptides. Such failures often can be the first cause of illness. Return to health can be relatively quick and easy, however, when the missing peptide(s) is reintroduced into the body because such peptides can, as described above, "instruct" cells to create more copies of the peptides. These are commonly called "proline-rich-polypeptides" (PRPs), "cytokine precursors" or "immuno-modulating peptides". Commonly, these peptides have been called the "software of the cell" or "software of the human operating system", which refer to the information required for all living mammalian cells to function. The initialization of correct cellular function is started when a female lactating mammal first delivers the "colostrum" to a newborn mammal baby, which commonly is called "passive immunity". In addition to such immunity, the colostrum also provides cytokine precursors to initiate many biochemical processes in mammalian cells. Thus, reintroduction of a small amount—perhaps a single copy—of one or more missing peptides to any infant, teenage, adult or elderly human, or any aged mammal, can quickly return cells in the body to their normal amount of the peptide(s) in question.

The target peptides can be derived from blood or from other mammalian bodily fluids derived from or in contact with blood. Such fluids include, but are not limited to, milk, colostrum, semen, urine, vaginal fluid, and the like. However, in materials such as milk and colostrum, for example, peptides are in what is essentially an impaired state because they are agglomerated with or on much larger biochemical macromolecules i.e. fats or other proteins. Additionally, ingestion by eating or drinking certainly denatures the peptides because of the acidic conditions of the stomach and the relatively aggressive enzymatic action of the digestive tract. Thus, although many external sources of peptide ligands are available, these peptides often are in a form that renders them useless for the desired effect. Accordingly, processing or refinement of such external sources is necessary.

Of the external sources of peptides, the one that seems to provide them in the highest concentrations and is most widely available is colostrum. This material has been the subject of numerous processing methodologies. However, almost all of the previously described processing methods appear to have been directed at collecting or isolating biologically active macromolecules that are much larger than peptides, such as, for example, proteins, lactoferrin, immunoglobulin, lipids, etc.

Importantly, present colostrum processing methods tend to encourage relatively high fluid pressures and much lower yields of peptides as a side effect of fast processing speeds and current technologies used. For those references dealing with ways to isolate large molecules such as immunoglobulin, lactoferrin, etc., this is not surprising because such macromolecules are relatively hearty and capable of withstanding such pressures. Peptides, however, respond quite differently to high processing pressures. In particular, many types of peptides can be denatured at pressures ranging from about 210 kPa (approximately 30 psi) to about 690 kPa (approximately 100 psi). For example, peptides involved in the prevention of viral infections are among those that can be denatured at the lower end of this range of pressures (less than 10 psi). The term "Denatured", with respect to a peptide, connotes an alteration or conformation change from the natural state due to, for example, physical forces (e.g., adhesion to another molecule(s), exposure to excessive temperature or pressure during processing, etc.), chemical reaction (e.g., scission due to exposure to excessively acidic or basic conditions), enzymatic, degradation, and the like.

Accordingly, there remains a need for a method of processing animal-derived fluids that result in an end product which is peptide-rich, with the same efficacy as in its native state, but substantially free from other materials that can denature such peptides, and thus able to fully express their peptide bioactivity without steric hindrance, and increase liquid diffusion of these peptides.

SUMMARY OF THE INVENTION

The present invention relates to a method and a system for processing mammalian bodily fluids, for example colostrum, to isolate target peptides and proteins. The mammal can be a bovine, for example a cow, goat, pig, buffalo, deer, or any other suitable mammal. For example, the present invention can process colostrum produced by lactating cows, but is not so limited. Notably, other mammals can be used to supply colostrum, or other mammalian fluids.

The method can include the steps of passing a mammalian bodily fluid through at least one ion exchange column or filter. The ion exchange column can include an anionic resin and/or a cationic resin. The ion exchange column or filter can be selected to remove large particles, for instance certain proteins, at a first pH level selected to remove such large particles at a maximum fluid pressure of 30 pounds per square inch (psi). In another arrangement, the maximum fluid pressure can be less than 10 psi. The large particles can be released from the ion exchange column or filter with a rinse solution having a pH selected for releasing the large particles.

The pH of the fluid then can be adjusted to be a value less than 5.0, and the fluid can be filtered with a microfilter having an initial pore size no greater than 300 nm or an ultrafilter having a pore size no greater than 20,000 Daltons. A pH of a retentate trapped by the filter can be adjusted to have a value between 6.5 and 7.0 and antibiotics can be washed from the retentate.

DETAILED DESCRIPTION OF THE PREFERRED EMBODIMENTS

The present invention relates to a method of isolating certain peptides and proteins from mammalian bodily fluids. In particular, the peptides and proteins can be isolated from the bodily fluids by filtering the bodily fluids using one or more filters having a relatively small average pore size, for example an average pore size of 1.4 μm or less. In one arrangement, the peptides and proteins being isolated can encounter a pressure that is equal to or less than 30 pounds per square inch (psi), and more preferably a pressure that is less than 10 psi. The peptides targeted for isolation can be, for example, proline-rich-peptides and/or non-ionic peptides. Such peptides are important in various biochemical processes. The proteins targeted for isolation can be, for example, alpha-lactalbumin, beta-lactoglobulin, lactoferrin, lactoperoxidase, IgS, and immunoglobulins such as IgG, IgA, and IgM, etc.

Blood and mammalian bodily fluids derived from blood, or in contact with blood, are potential sources for the target peptides and proteins. For example, colostrum, milk, semen, urine, vaginal fluid, and the like can be used as a source of the target peptides and proteins. Advantageously, colostrum has relatively high levels of lactoferrin, immunoglobulins, and peptides, and colostrum is produced in relatively large quantities. Thus, for purposes of the following description of the isolation process, colostrum is used as a representative starting material. It should be noted, however, that the present invention is not so limited in this regard.

Figure 1:
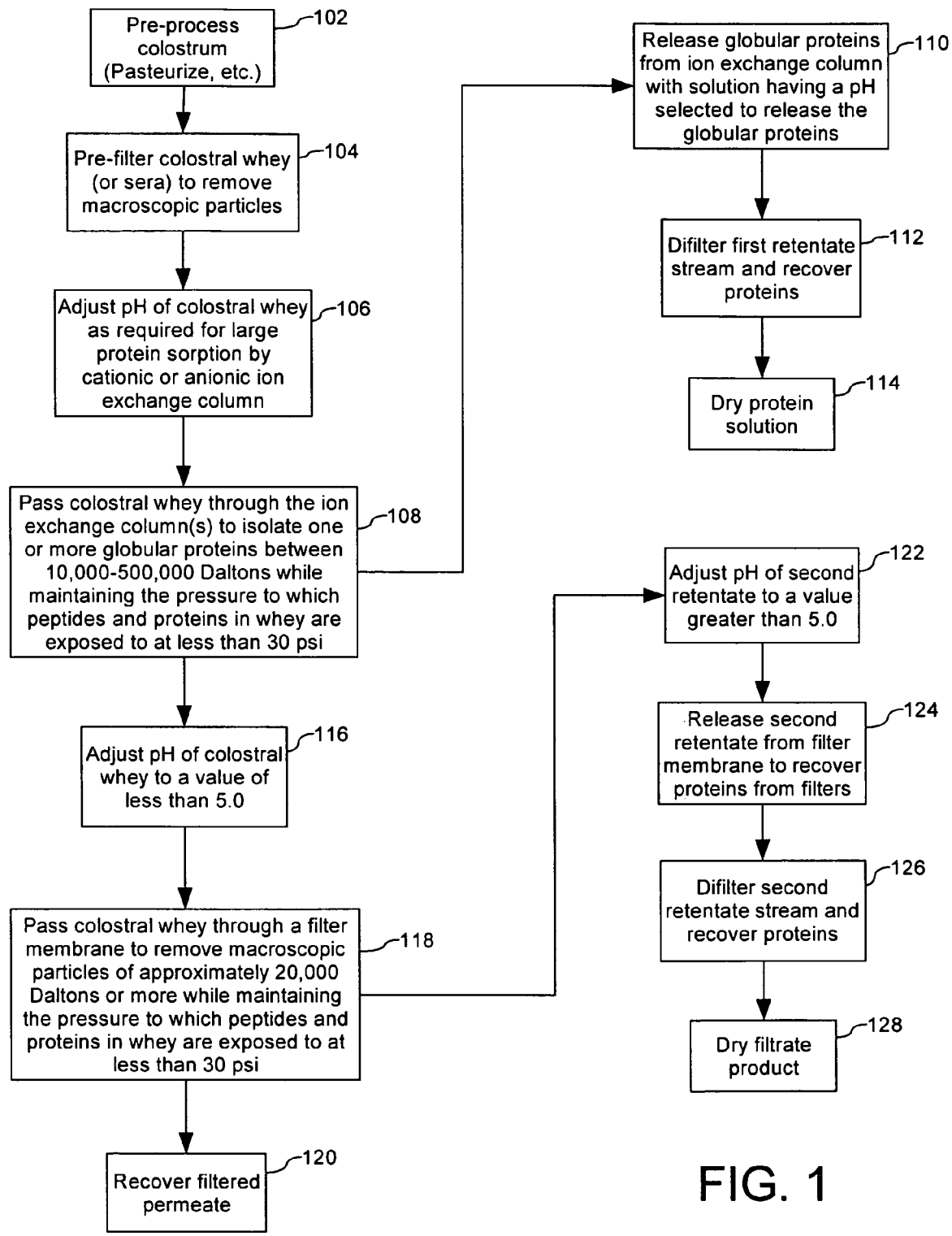
FIG. 1 is a flow chart of a process which is useful for understanding the present invention.

FIG. 1 presents a method 100 which is useful for understanding a method for processing colostrum. The first colostrum withdrawn from a given mammal usually has a larger amount of the target proteins and peptides (per unit volume) than any subsequent colostrum collected from the same mammal. Thus, the first and second milking of a particular mammal can provide a higher yield of the desired peptides in comparison to subsequent milkings. Although the production of the target peptides and proteins is not affected by the use of dairy cows which have had their utters specially treated with antibiotics or antigen-like materials that have more than a 30 day withholding period, the use of such dairy cows is not preferred because of potential contamination of the colostrum with antibiotics. Nonetheless, if such dairy cows are used, the antibiotics or materials can be removed from the colostrum using filtration technologies.

Referring to step 102, the colostrum can be pre-processed. For instance, the colostrum can be collected and stored under suitable storage conditions. Specifically, the colostrum preferably is collected under conditions that prevent gross contamination by bacteria. For example, the collection and storage conditions can be those which are appropriate for the storage of milk for human consumption. For instance, the conditions can be consistent with applicable governmental (e.g., USDA) guidelines.

Where pumps are employed in a given step, they preferably are of a type that does not have impellers or other features capable of producing a shearing effect. In the design of a specific process, each aspect preferably is considered and tailored to prevent damage to the target peptides and proteins. Once the raw colostrum farm tank has been emptied the tank can be cleaned with an automatic CIP system through a spray ball. The use of a tank that does not have sharp corners can be used to facilitate cleaning of the tank and minimize build up of colostrum in the corners of the tank.

During processing, it is preferred that the fluid pressures which are experienced by the target peptides at each part of the process stay equal to, or below, 30 psi. For example, keeping the fluid pressures experienced by the target peptides at or below about 10 psi can minimize denaturing of the target peptides. To provide these relatively low operating pressures while maintaining industrially acceptable processing speeds, running the process in the form of a batch (as opposed to continuously) can be preferable. Where batch processing is used, typical amounts can range from about 375 to about 37,500 L (100 to 10,000 gallons), depending on down-line processing speed.

There can be a further benefit by immediately placing the raw material under refrigeration. For example, cooling the raw material to less than 45 degrees Fahrenheit in less than 4 hours can reduce bacterial growth in colostrum. Any suitable cooling technique can be used to cool the raw material. For example, inline plate heat exchangers or chilled water systems can be used to immediately cool the colostrum to a desired temperature. Still, the invention is not so limited and other cooling methods can be used.

Freezing of colostrum, as well as other types of raw material, reduces the efficacy or concentration of the natural peptides and is therefore not desired because many of the peptides and globular proteins can be damaged by the freezing of the water within the raw material. In particular, water crystals formed when the colostrum is frozen can cut through the proteins, and thus increase the degree of denaturing. This can reduce the yield of target peptides and proteins from the raw material. Nevertheless, although the use of previously frozen colostrum is not optimal, it still can be used and is within the intended scope of the present invention.

Processing of the colostrum can be performed proximate to or remote from the point of collection. In the case that processing is performed remote to the point of collection, transportation of the raw material preferably occurs under conditions suitable for handling of the raw material without significant denaturing of the target peptides and proteins and without excessive bacterial growth. For example, the raw material can be transported using methods known to those skilled in the art.

Testing can be performed on the colostrum to measure the concentration of target proteins and/or target peptides within the raw material. For example, when attempting to collect colostrum from a mammal, an amount of milk may also be collected. Since milk can have a lower concentration of the target peptides and proteins than colostrum, greater milk content within the raw material can lower the yield of the target peptides and proteins from the raw material. Specific gravity testing can be used to measure the amount of milk present in the raw material, and thus provide an indication of the quality of the raw material for the intended purpose. Other methods also can be used to indicate the quality of the raw material. For example, high-pressure-liquid-chromatography, radial immunodiffusion (RID) assay, and/or enzyme-linked immunosorbent assay (ELISA) can be used to accurately determine the levels of immunoglobulins present in the raw material. The testing of the raw material can be implemented as part of a quality control program.

The amount of colostrum collected from a cow can be limited to no more than approximately 15 L (4 gallons), collected within the first 24 hours after birth. In the case that the colostrum is transported to a processing facility remotely located from the location of the colostrum collection, it can be advantageous to maintain the colostrum below about 45 degrees Fahrenheit (7 degrees Centigrade) at all times to prevent excessive bacteria growth, but it is preferred that freezing of the colostrum be avoided to prevent denaturing of the proteins and peptides. Further, it also can be advantageous to process the colostrum soon after collection to insure a high quality product.

For example, it is preferred that the colostrum arrive at the processing facility within 72 hours of collection. The colostrum can be pasteurized using an automated legal high temperature short residence time (HTST) pasteurizing system, or ultra-high temperature (UHT) pasteurizing system, but preferably not batch pasteurized. The raw material can be stored in a suitable storage container for processing. For example, the storage container can be a tank made of a relatively inert material, such as stainless steel.

The process also can isolate colostral whey or colostral sera from the colostrum for further processing. Colostral whey can be derived from separation technologies from any pre-curing of the colostrum. Colostral sera can be derived from separation technologies from any non-curing processes of the colostrum. When colostrum is collected from more than one mammal, the colostrum can be stirred with some type of stirring mechanism, for example a paddle or stirrer blades, or a pumping motion, to gently mix the raw material. Where stirrer blades are used as the stirring mechanism in the preceding step, slow rotation of the blades and a backward angling of the blades can provide a gentle mixing to minimize damage to peptides and proteins. Where pumping is used as the stirring mechanism in the preceding step, slow rotation of the impellers with low shear impeller designs can provide a gentle mixing to minimize damage to peptides and proteins.

Such mixing can help to counter inconsistencies between colostrum from the different mammals and to provide a more uniform temperature. For example, because a particular cow might be deficient in one or more particular peptides, a blending of colostrum from many cows can provide a given colostral blend that contains all of the target peptides and proteins. Further, both cow and heifer colostrum can be mixed together. Colostrum containing blood of non-genetically modified mammals typically does not have a high concentration of the target peptides, however.

After blending, the colostrum blend can be moved to a first phase of a reduction process which involves separating and removing much fat from the colostrum. Various means, such as separators, centrifuges, chemical, hydrophobic, supercritical $CO_2$ or liquid-liquid extractions are available to accomplish this task.

The defatted blend can be conveyed to a curdling vessel (e.g., a stainless steel tank) where it can be gently stirred. During this process the temperature of the defatted blend can be raised to between about 90 degrees Fahrenheit (32 degrees Centigrade) and about 99 degrees Fahrenheit (37 degrees Centigrade) in preparation for curdling. Curdling involves the coagulation of the majority of solids remaining in the blend (principally casein). It generally is accomplished by addition of rennin, an enzyme-rich extract from the stomachs of calves, or an acid such as HCl to the warmed colostrum blend. Once the rennin or acid is added, a curd gradually begins to form soon after stirring of the blend is stopped. As the curd forms, it rises to the surface, producing a soft white cake or crust sitting or floating on whey. The whey, which is the desired product from this step, can be drained away from the curdling vessel. Alternatively, a defatted colostrum stream can be microfiltered and/or ultrafiltered instead of curding to extract the same peptides.

The remaining curd can be cut into small pieces by, for example, activating a stirring mechanism in the tank. The broken curd can be conveyed away from the tank through pipes made of an inert material, for example stainless steel, to a large screen, which also can be made from a relatively inert material. Any whey trapped in the curd can pass through the screen and, optionally, can be added into the whey collected previously. (The curd can be collected for sale or discarded, as desired.)

Proceeding to step 104 of FIG. 1, the collected whey or sera can be passed through a fines reducer or a clarifier to exclude more of the small pieces of curd which may be conveyed away from the curdling vessel during removal of the whey. This additional step, although certainly not required, can be beneficial because it increases the service interval for the filter media described below. The whey can be conveyed to the next step of the reduction process through, for example, stainless steel pipes.

Figure 2:
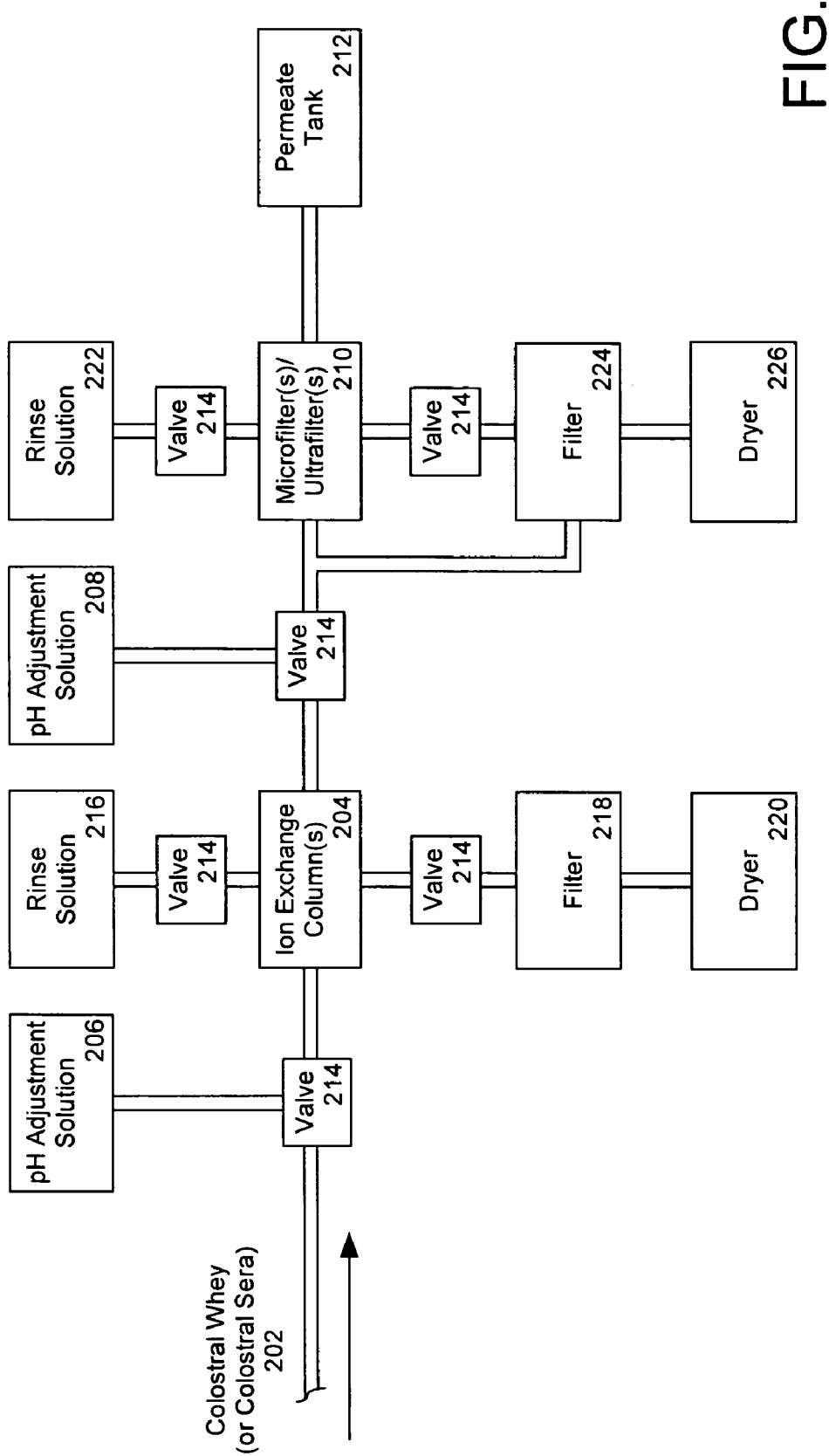
FIG. 2 is a block diagram of a processing system which is useful for understanding the present invention.

Making reference to the processing system 200 of FIG. 2, the pre-processed colostral whey (or colostral sera) 202 can undergo further processing using ion exchange chromatography to isolate desired proteins from the colostral whey 202. Proceeding to step 106 of FIG. 1, the pH of the colostral whey 202 can be adjusted as required for large protein sorption by one or more ion exchange columns 204, which can be a cationic ion exchange column or an anionic ion exchange column. The ion exchange column 204 can comprise resin, which can be in the form of a bead of uniform size or with a wide standard deviation of sizes, or a non-spherical shape of similar or varying sizes. For example, a cationic resin can be an SP or SM type resin, and an anionic resin can be a QEA or Q type resin. Such resins are known to those of ordinary skill in the art. The resin can be packed with adequate bulk density or contained within a containment vessel so as to allow adequate flow of the colostral whey 202.

A pH adjustment solution 206 can be added to the colostral whey 202 until a suitable pH of the colostral whey 202 is reached. Notably, the pH of the colostral whey 202 can affect the surface chemistry of proteins contained within the colostral whey 202, and give the surface of the proteins a net negative charge, a net positive charge, or a net neutral charge. A suitable acid for lowering the pH of the colostral whey 202 can be, for example, food grade citric acid, phosphoric acid, or lactic acid. Alternatively, a suitable base can be added to the whey to raise the pH. Examples of suitable bases are potassium hydroxide, calcium hydroxide and sodium hydroxide, but the present invention is not limited in this regard. Notably, the use of potassium hydroxide adds potassium to the colostrum, which protects proteins during a subsequent pasteurization process, if such a process is used. A suitable valve 214 and/or suitable mixing pumps (not shown) can be used to mix the pH adjustment solution 206 with the colostral whey 202.

Continuing at step 108, the colostral whey 202 can be passed through the ion exchange column 204 at a pressure less than or equal to 30 psi, and more preferably below 10 psi, to isolate one or more globular proteins between 10,000 and 500,000 Daltons. For example, such proteins can include alpha-lactalbumin, beta-lactoglobulin, lactoferrin, immunoglobulins and other whey proteins. A cationic ion exchange column can comprise a positive resin. In consequence, lactoferrin and lactoperoxidase can be sorbed when the pH of the whey solution is between about 6.5-7.0. Moreover, all whey proteins can be sorbed within the cationic ionic exchange column when the pH is less than 4.0. For instance, the pH can be in the range of about 3.0 to 4.0. An anionic ion exchange column can comprise a negative resin. In this arrangement, all whey proteins can be sorbed when the pH of the whey solution is between about 6.5-7.0. Typically, little or no proteins are sorbed in an anionic exchange column when the pH of the solution is less than 4.0.

Proteins sorbed in the resin are globular proteins that typically do not bind to the resin. Since the proteins do not bind to the resin, the proteins can be recovered from the ion exchange unit 204 by passing a rinse solution 216 having a pH selected to release the proteins, as shown in step 110. In particular, the rinse solution 216 can change the charge of the resin in the ion exchange column 204 and cause the resin to release the proteins into a retentate stream. Solutions also can be used to change the net charge of the surface of the proteins so that the proteins repel the cationic or anionic resins. Proceeding to step 112, the retentate stream with the liberated proteins then can be difiltered to remove any salts that may remain in the solution. For example, the retentate stream can be passed through one or more filters 218 which have pore sizes greater than the globular proteins in the retentate stream. The retentate stream then can be dried to recover the globular proteins, as shown in step 114. For instance, the proteins can be concentrated to between 15-30% total solids. The proteins then can be passed through a dryer 220 and subjected to freeze or low-heat indirect steam spray drying. An evaporator can be used to concentrate further the retentate stream. Suitable valves 214 and/or suitable fluid pumps (not shown) can be used to control fluid flow within the system 200.

Advantageously, the whey or sera need not be subjected to fluid pressures in excess of normal bodily fluid pressures in this process, thus preserving the native states of the proteins and peptides contained in the whey. The resulting filtrate or flow-through stream therefore can be more effective in cellular interactions in comparison to a filtrate filtered at pressures which are significantly higher than the pressures the bodily fluids experience within the mammal from which they are extracted. Also, the yield of non-ionic peptides from the whey or sera using ion exchange technologies, as will be described below, can be between 80-85% when compared to the original number in the raw colostrum liquid. When membrane filtration techniques are exclusively used to isolate the proteins, a peptide yield of about 45-50% can be expected. This is a significant yield improvement over existing extraction technologies.

In the foregoing step, to achieve adequate separation while maintaining operating pressures at or below about 30 psi, for example below about 10 psi, relatively short filtration units can be used to minimize back pressure. For example, the filtration units can be on the order of about 0.3 m to 1.5 m in length ion exchange columns with fixed beds, packed beds or expanded bed designs, having bed depths not exceeding 20 cm to 25 cm, thus minimizing the pressure drop across the bed, preferably less than 5 psi. Notably, dynamic or moving ion exchange beds do not have such pressure drops. However, the yield can be less with dynamic beds as compared to static or fixed beds. Specifically, there can be a higher concentration of proteins in the whey using dynamic beds as compared to exposing the stream of whey to fresh resin in lower sections of a fixed bed.

In one arrangement, two or more ion exchange columns can be cascaded in series. The use of cascaded ion exchange columns provides a longer contact time for the flow-through protein solution. Moreover, multiple ion exchange columns can be connected in parallel to increase throughput and scalability of a commercial ion exchange process. Ion separation technologies as described herein can be used before or after the filtration steps as needed to purify individual or multiple protein streams, depending on the order in which it is desired to remove the proteins. Notably, the order of ion exchange and filtration does not affect production of desired peptides.

Although not critical to the present process, the diameter of the fixed ion exchange beds can be minimized, for example to less than 30 cm, to prevent uneven bed depths of resin across the resin bed to minimize "uneven lateral resin migration". Minimizing the lateral resin migration can help to maintain a uniform pressure drop through the ion exchange bed.

In lieu of ion exchange columns 204, tangential flow (sometimes called cross-flow) filters can be used; tubular microfilter unit also can be used. Tangential or cross flow filtration is generally preferred over dead-end filtration because the latter can result in unacceptable pressures unless throughput speeds and volumes are kept quite low. Additionally, tangential flow units do not result in all particles being trapped in the filter membrane, i.e., certain large particles merely pass along the exterior of the membrane and never get retained in a pore; this extends the operation period for a given filter unit.

Microfilters as a class generally are used to remove substances that range in size from about 0.1 to about 1.4 µm. By selecting a filter with an average pore size of from 0.1 to 0.45 µm, one can achieve the desired result of removing most materials having a molecular weight of approximately 500,000 Daltons or more, which includes almost all bacteria but very few proteins. In fact, proteins the size of antibodies and smaller pass through this size of filter pore with the greater portion of the water present in the whey.

Microfilter membranes can be made from a wide variety of materials and are commercially available from numerous sources. Membranes can have inner permeate tube diameters of about 0.05 inch to 2.0 inches and outer diameters of about 1.0 inch to 12.0 inches. Acceptable microfilters for such units include, for example, ceramic filters, metallic, Teflon, polyethylsulphone (PES) (other polymeric spiral wound), tubular, polyplastic membranes, etc.

The colostral whey (or colostral sera) 202 can be conveyed, again preferably by inert means such as stainless steel pipes, to the next step in the reduction process. Here, suspended materials that range in size down to that which can be seen only with a relatively powerful microscope can be removed, for example those particles greater in size than 100,000 Daltons. Referring to step 116, the pH of colostral whey 202 again can be adjusted with a pH adjustment solution 208. For instance, a suitable base or suitable acid can be added to the colostral whey 202 until the pH is in the range from about 4.5 to about 5.0. Although not required, it is preferable that the pH be in the range from about 4.55 to about 4.70, and most preferably of about 4.6. This slightly acidic pH has been found to be sufficient to kill or disable most bacterium that might have made its way through the processing or that might have been in the container used to hold the filtrate product. The need for preservatives and anti-bacterial, yeast and mold inhibitors can therefore be reduced or eliminated.

Continuing at step 118, the twice pH adjusted colostral whey 202 can be passed through microfilter(s) and/or ultrafilter(s) 210 to remove macroscopic particles of approximately 20,000 Daltons or more while maintaining the pressure to which the remaining proteins and peptides in the colostral whey are exposed to at less than 30 psi. For instance, an exemplary separation process which implements a tangential flow unit having an ultrafilter membrane. Nanofiltration or reverse osmosis also can be used. However, nanofiltration and reverse osmosis can be expensive and typically require higher operating pressures than ultrafiltration. In either case, tangential flow filtration can result in lower operating pressure than dead-end filtration.

A tangential flow ultrafilter unit can be similar in design to the previously described microfilter unit, except that its filter can have smaller pores. For example, the average pore size of this type of filter can range from about 1,000 to about 100,000 Daltons. An ultrafilter for such a unit can include, for example, a spiral wound filter (Kock; Osmonics-Desal, Synder, PTI, Pall). The membranes of the filter can be made of cellulosic materials, fluoropolymers, polysulfones, or any other suitable material.

In some instances, the acidic pH of the liquid will cause the pore sizes of polymer or non-rigid plastic filter membranes to shrink. For instance, a pH of 4.6 can cause the pores of certain microfilter membranes having an initial pore size greater than 120,000 Daltons to shrink to 50,000 Daltons, or smaller. For example, the average pore size can be in the range from 300 nm to 450 nm (0.3 µm to 0.45 µm). A preferred average pore size after shrinkage is from 15,000 to about 30,000 Daltons, with 20,000 Daltons being a highly preferred average pore size. Use of such relatively small pores with acidic pHs, as described, results in the removal of most proteins (including antibodies) and endotoxins, which might have been included in the original colostral blend. More particularly, transmission of the antibiotic residues through the membrane is inhibited, and the residues thus remain in the retentate. In consequence, the acidic permeate that is produced is free from antibiotic residues and thus can be used as a good source of proline-rich-polypeptides.

In the two preceding reduction (i.e., filtration) steps, the temperature of the ion exchange columns and filtration units can be maintained as high as about 52 degrees Centigrade, primarily to control bacterial growth. Alternatively, process temperatures for all unit operations can be maintained to be no higher than 0.50 to 5 degrees Centigrade. Use of such relatively low temperatures has been found to keep any fat remaining in the whey in macroscopic globules that do not even enter, and thus occlude, the pores of the filters. The low temperature also maintains low growth of microbes in the process lines and fluids. Nevertheless, the invention is not limited in this regard and any other suitable temperatures can be used. The antibiotic free permeates then can be collected as products and set aside from further Ion exchange separations.

Where the ultrafiltration step employs a filter having an average pore size of no more than about 20,000 Daltons, the filtrate product is essentially free of proteins, peptides, and biochemical macromolecules that have a molecular weight of 20,000 Daltons or greater. For example, antibiotics, such as penicillin G, will be removed from the filtrate product during the ultrafiltration step. More preferably, the filtrate product is essentially free of peptides or proteins having molecular weights of about 10,000 Daltons or greater, and most preferably at least 90% of the component peptides of the filtrate product have molecular weights of no more than about 2,500 Daltons. This is important for several reasons, one of which is that the filtrate then is substantially free of molecules that can act as points of agglomeration for the desired peptides. A peptide that has agglomerated to other peptides or to larger proteins usually is denatured. Similarly, peptides subject to bacterial-induced enzymatic degradation also can be denatured and, accordingly, the filtrate product preferably is essentially free of such bacteria. Moreover, the filtrate product preferably has no more than about 10% of its component peptides in a denatured state. Even lower concentrations of denatured peptides are desirable.

Proceeding to step 120, this antibiotic free low pH filtered permeate (filtrate product) can be collected in a permeate tank 212 until the flow rate drops significantly and used for further processing as liquid or powder colostrum products. The resulting antibiotic free low pH permeate (filtrate product) which passes through the microfilters and/or ultra filters can be collected until the flow rate drops significantly and used for further processing as liquid or powder colostrum products.

Although not essential, the filtrate product can be further preserved by adding food grade 0.1% EDTA to inhibit bacterial growth and 0.1% Potassium Sorbate to minimize any yeast and mold from growing in the final product, or hydrogen peroxide, or some other suitable preservative. If desired, the filtrate product may have the flavor profile changed by adding a flavor ingredient such as vanilla, chocolate, strawberry, pina-colada, etc. This may make the filtrate product more palatable as an ingested liquid, spray, capsule, or lozenge. If the filtrate is to be used as topical liquid or topical spray only, scent could be added to the filtrate. As a final treatment the filtrate product can be further filtered one or more times using a filter not more than 0.45 µm to catch any potential remaining microbes. The filtrate then can be aseptically packaged. At all stages of the processes Good Manufacturing Practices (GMPs) should be followed to preserve the integrity of the final filtrate product.

Each milliliter of filtrate product preferably includes at least 0.3 g of total protein, more preferably at least 0.35 g protein. Most preferably, each milliliter of product contains from 0.36 to 0.38 g of peptides. Although this amount seems small, it has been found to provide a full (or very nearly full) array of target peptides, thus providing maximum benefit to the human or animal which receives a dose thereof.

At this point it should be noted that the ion exchange separation technologies as described herein can be used before or after the filtration steps. Indeed, the ion exchange and filtration steps can be implemented as required to achieve desired protein streams, depending on the order one wishes to remove these proteins. However, the process technology order is irrelevant with respect to the final filtrate product because the desired peptides are not affected by the order in which the colostral whey 202 is processed by the ion exchange columns 204 or filters 210.

In the present example, the retentate next can be collected from the microfilters/ultrafilters. At step 122, the pH of the retentate collected in the microfilters and/or ultra filters can be adjusted to be above 5.0, and preferably in the range 6.5 to 7.0. The pH can be adjusted using a basic solution. For example, a typical commercial food grade calcium hydroxide, potassium hydroxide and/or sodium ammonium hydroxide can be used to adjust the pH of the retentate. At step 124, the retentate can be released from the microfilter(s) and/or ultrafilter(s) 210 with a rinse solution 222 to recover filtrate product from the filters 210. The rinse solution 222 can be a salt solution or other suitable permeate stream with some ionic strength to wash antibiotics from the retentate. Proceeding to step 126, the retentate stream with the liberated filtrate product then can be difiltered to remove any salts that may remain in the solution. For example, the retentate stream can be passed through one or more filters 224 which have pore sizes greater than the filtrate product in the retentate stream.

Experiments have shown that washing the retentate with an ionic solution at neutral pH and three times the volume of the retentate was sufficient to reduce the antibiotic levels to less than 5 ppb for all types of penicillins, which is below the United States Department of Agriculture (USDA) maximum level for acceptable milks. Moreover, the rinse solution 222 circulated to repeat the washing cycle, which can help to further reduce the antibiotic levels. In one arrangement, the rinse solution 222 can be a waste stream from another dairy process. The wash/difilter process can be repeated until the antibiotics reach a low enough level. The rinse stream which passes through the microfilters and/or ultra filters can be collected until the flow rate drops significantly, and discarded as a waste product.

The retentate then can be dried to recover the filtrate product, as shown in step 126. For instance, the filtrate product can be passed through a dryer 226 and subjected to freeze or low-heat indirect steam spray drying. An evaporator can be used to concentrate further the filtrate product. Again, suitable valves 214 and/or suitable fluid pumps (not shown) can be used to control the fluid flow. All stages in the process can adhere to a Hazard-Analysis and Critical-Control Program (HACCP) and Good Manufacturing Processes (GMPs) consistent with the recommended procedures of the USDA and Food and Drug Administration (FDA).

The mammal which produces the raw material used for processing can be a mammal which has immunity to an antigen. For example, the mammals can be genetically engineered. Nonetheless, the invention is not limited in this regard as the mammal can be non-genetically engineered. The mammal can be rendered immune by injecting an antigen or a protein specific for the antigen into the mammal. In another arrangement, the mammal can be exposed to the antigen before the mammal commences lactation. The antigen can be a virus or can be derived therefrom. For example, the virus can be the Human Immunodeficiency Virus (HIV, type 1 or type 2). The virus also can be a planar warts virus, an influenza virus, a cold virus, or any other virus.

Exposure by the mammal producing the raw material to the virus can result in peptides and proteins being produced which can be used to fight ailments. Accordingly, the filtrate product can be administered to maintain wellness or to induce recovery from a wide range of infectious and progressive disease processes. For example, the filtrate product can be used to treat Allergies, Arthritis, Benign Prostatic Hyperplasia (such as the inflammatory aspect), Cancer (for example for adjunctive use), Celiac Sprue, Crohn's Disease, Diabetes Type II, Hypertension, Lupus (Discoid and Systemic), Multiple Sclerosis, Perthes Disease (Active), Premenstrual Syndrome and Endometriosis, Prion Disease (Kuru and Creutzfeld-Jakob Syndrome), Psoriasis, Sjogren's Syndrome, Spinal Muscular Atrophy, Thrombocytopenia (Ideopathic and Autoimmune), Topical Applications (burns, wounds, infections, insect bites, diaper rash and Herpetic Lesions), Acute Viral Infections, and numerous other ailments. Further, peptides and proteins isolated from the raw material can be used to treat digestive problems. Still, there are a number of other medical uses for such proteins, and the invention is not so limited.

The above list of conditions and diseases are simply a sample of what can be treated indirectly by a course of peptide treatment, and is by no means limiting. Moreover, in recent years, peptide treatment has been found to be beneficial for a wide variety of ailments. In the peptide treatment of non-viral diseases or conditions, for example, it is believed that the peptides can be used to provide correct information to cells for mammal cellular function, and thus better prepare the cells for the treatment of the conditions and diseases. In viral treatments, the peptides can act as protectors to the cellular surface by preventing the viral ligand proteins from attaching to a receptor on a cellular surface.

The product can be administered as an oral spray or held in the mouth for no less than 30 seconds to allow sorption through the mucous membrane of the mouth. (For adults, with non-viral infections the composition is typically administered twice a day wherein each administration consists of five successive 1 mL sprays; for children, the composition is preferably administered twice a day wherein each administration consists of two or three 1 mL sprays; for infants, the composition preferably is administered twice a day wherein each administration consists of one 1 mL spray. For adults, with viral infections the composition is typically administered every four hours wherein each administration consists of five successive 1 mL sprays; for children, the composition is preferably administered every four hours wherein each administration consists of two or three 1 mL sprays; for infants, the composition preferably is administered every four hours wherein each administration consists of one 1 mL spray.) Other administration routes include, without limitation, injection, topical application, intraocular application, nebulization or atomization, and the like. For example, a topical application of the composition might be indicated when treating a burn or wound.

The following examples represent potential uses for peptides isolated using the above process for treating a number of different medical conditions. It should be noted that the isolated peptides can be used for numerous other treatments and the examples listed are by no means exhaustive.

EXAMPLES

| | |
|---|---|
| Example 1: | Allergies |
| Typical dose: | three sprays (5 ml). |
| Typical administrations per day: | 2 |
| Typical interval of initial response: | 1–3 days |
| Typical interval to benefit plateau: | 3–7 days |
| Typical response: | 2–3 days |
| No reduction or elimination of other therapeutics until justified by condition of patient. | |
| Example 2: | Arthritis |
| Typical dose: | three sprays (5 ml). |
| Typical administrations per day: | 2 |
| Typical interval of initial response: | 7-21 days |
| Typical interval to benefit plateau: | 42-56 days |
| Typical response: | 2-3 days |
| No reduction or elimination of other therapeutics until justified by condition of patient. | |
| Example 3: | Benign Prostatic Hyperplasia (inflammatory Aspect) |
| Typical dose: | three sprays (5 ml). |
| Typical administrations per day: | 2 |
| Typical interval of initial response: | 7-14 days |
| Typical interval to benefit plateau: | 14-28 days |
| Typical response: | 2-3 days |
| No reduction or elimination of other therapeutics until justified by condition of patient. | |
| Example 4: | Cancer (Adjunctive use only) |
| Typical dose: | three sprays (5 ml). |
| Typical administrations per day: | 2 |
| Typical interval of initial response: | 7-14 days |
| Typical interval to benefit plateau: | n/a |
| Typical response: | 2-3 days |
| No reduction or elimination of other therapeutics until justified by condition of patient. | |
| Example 5: | Celiac Sprue |
| Typical dose: | three sprays (5 ml). |
| Typical administrations per day: | 2 |
| Typical interval of initial response: | 1-3 days |
| Typical interval to benefit plateau: | 3-7 days |
| Typical response: | 2-3 days |
| No reduction or elimination of other therapeutics until justified by condition of patient. | |
| Example 6: | Crohn's Disease |
| Typical dose: | three sprays (5 ml). |
| Typical administrations per day: | 2 |
| Typical interval of initial response: | 7-14 days |
| Typical interval to benefit plateau: | 42-56 days |
| Typical response: | 2-4 days |
| No reduction or elimination of other therapeutics until justified by condition of patient. | |
| Example 7: | Diabetes Type II |
| Typical dose: | three sprays (5 ml). |
| Typical administrations per day: | 2 |
| Typical interval of initial response: | 1-7 days |
| Typical interval to benefit plateau: | 14-28 days |
| Typical response: | 2-3 days |
| No reduction or elimination of other therapeutics until justified by condition of patient. | |
| Example 8: | Hypertension |
| Typical dose: | three sprays (5 ml). |
| Typical administrations per day: | 2 |
| Typical interval of initial response: | 7 days |
| Typical interval to benefit plateau: | 28-56 days |
| Typical response: | 2-3 days |
| No reduction or elimination of other therapeutics until justified by condition of patient. | |
| Example 9: | Lupus (Discoid and Systemic) |
| Typical dose: | three sprays (5 ml). |
| Typical administrations per day: | 2 |
| Typical interval of initial response: | 7-14 days |
| Typical interval to benefit plateau: | 28-58 days |
| Typical response: | 2-3 days |
| No reduction or elimination of other therapeutics until justified by condition of patient. | |
| Example 10: | Multiple Sclerosis |
| Typical dose: | three sprays (5 ml). |
| Typical administrations per day: | 2 |
| Typical interval of initial response: | 7-28 days |
| Typical interval to benefit plateau: | 28-180 days |
| Typical response: | 2-3 days |
| No reduction or elimination of other therapeutics until justified by condition of patient. | |
| Example 11: | Perthes Disease(Active) |
| Typical dose: | three sprays (5 ml). |
| Typical administrations per day: | 2 |
| Typical interval of initial response: | 1-2 days |
| Typical interval to benefit plateau: | 7-28 days |
| Typical response: | 3-4 days |
| No reduction or elimination of other therapeutics until justified by condition of patient. | |
| Example 12: | Premenstrual Syndrome and Endometriosis |
| Typical dose: | three sprays (5 ml). |
| Typical administrations per day: | 2 |
| Typical interval of initial response: | 1-2 days |
| Typical interval to benefit plateau: | 14 days |
| Typical response: | 2-4 days |
| No reduction or elimination of other therapeutics until justified by condition of patient. | |
| Example 13: | Prion Disease (Kuru and Creutzfeld-Jakob Syndrome) |
| Typical dose: | three sprays (5 ml). |
| Typical administrations per day: | 2 |
| Typical interval of initial response: | 12-28 days |
| Typical interval to benefit plateau: | 28-56 days |
| Typical response: | 2-3 days |
| No reduction or elimination of other therapeutics until justified by condition of patient. | |
| Example 14: | Psoriasis |
| Typical dose: | three sprays (5 ml). |
| Typical administrations per day: | 2 |
| Typical interval of initial response: | 3-7 days |
| Typical interval to benefit plateau: | 28-56 days |
| Typical response: | 2-3 days |
| No reduction or elimination of other therapeutics until justified by condition of patient. | |
| Example 15: | Sjogren's Syndrome |
| Typical dose: | three sprays (5 ml). |
| Typical administrations per day: | 2 |
| Typical interval of initial response: | 7-14 days |
| Typical interval to benefit plateau: | 14-28 days |
| Typical response: | 3-4 days |
| No reduction or elimination of other therapeutics until justified by condition of patient. | |
| Example 16: | Spinal Muscular Atrophy |
| Typical dose: | three sprays (5 ml). |

-continued

| | |
|---|---|
| Typical administrations per day: | 2 |
| Typical interval of initial response: | 7-14 days |
| Typical interval to benefit plateau: | 180 days |
| Typical response: | 2-3 days |
| Increased consumption of water should be encouraged in adult patients with this disease | |
| Example 17: | Thrombocytopenia (Ideopathic and Autoimmune) |
| Typical dose: | three sprays (5 ml). |
| Typical administrations per day: | 2 |
| Typical interval of initial response: | 1-2 days |
| Typical interval to benefit plateau: | 4-10 days |
| Typical response: | 3-4 days |
| No reduction or elimination of other therapeutics until justified by condition of patient. | |
| Example 18: | Topical Applications (burns, wounds, infections, insect bites, diaper rash and Herpetic Lesions) |
| Typical method of administration | Spray or apply with a sterile pad to affected area. |
| Typical administrations per day: | three sprays (3-5 ml) |
| Typical interval to initial response: | 4-24 hours |
| Typical interval to benefit plateau: | Variable with condition |
| Typical response: | 3-4 days |
| Typical observations include accelerated healing and reduced tendency to scar. | |
| Example 19: | Acute Viral Infections |
| Typical dose: | three sprays (2 ml). |
| Typical administrations per day: | 6 (every four hours) |
| Typical interval of initial response: | 4-24 hours |
| Typical interval to benefit plateau: | 2-7 days |
| Typical response: | 3-4 days |
| No reduction or elimination of other therapeutics until justified by condition of patient. | |
| Example 20: | Chronic Viral Infections (including HIV and SARS) |
| Typical dose: | three sprays (2 ml). |
| Typical administrations per day: | 6 (every four hours) |
| Typical interval of initial response: | 4-24 hours |
| Typical interval to benefit plateau: | 2-7 days |
| Typical response: | 3-4 days |
| No reduction or elimination of other therapeutics until justified by condition of patient. | |

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

The invention claimed is:

1. A method for separating the proline-rich polypeptides essentially free of peptides and proteins of about 10,000 Daltons or greater from the globular proteins having a molecular weight of between 10,000 and 500,000 Daltons in bovine colostrum, the method comprising the steps of:

(a) subjecting at least a portion of a bovine colostrum sample to at least one separation procedure comprising an ion exchange separation to yield separated proline-rich polypeptides essentially free of peptides and proteins of about 10,000 Daltons or greater and separated globular proteins having a molecular weight of between 10,000 and 500,000 Daltons, wherein no more than about 10% of the separated proline-rich polypeptides are denatured; and (b) collecting the separated proline-rich polypeptides;

wherein at least 90% of the separated proline-rich polypeptides have a molecular weight of no more than about 2,500 Daltons.

2. The method of claim 1, wherein the step (a) is performed at a pressure of 30 psi or less.

3. The method of claim 1, wherein the step (a) is performed at a pressure of 10 psi or less.

4. The method of claim 1, wherein the at least one separation procedure further comprises a size exclusion separation.

5. The method of claim 1, wherein the step (a) comprises changing the pH of the at least a portion of the colostrum.

\* \* \* \* \*